(12) United States Patent
D'Silva et al.

(10) Patent No.: US 6,258,973 B1
(45) Date of Patent: Jul. 10, 2001

(54) PROCESSES FOR PREPARING PESTICIDAL INTERMEDIATES

(75) Inventors: Themistocles D. J. D'Silva, Chapel Hill, NC (US); Jean-Erick Ancel, Saint-Genis-Laval (FR)

(73) Assignee: Rhone-Poulenc Agro, Lyons (FR)

( * ) Notice: Subject to any disclaimer, the term of this patent is extended or adjusted under 35 U.S.C. 154(b) by 0 days.

(21) Appl. No.: 09/572,948

(22) Filed: May 17, 2000

Related U.S. Application Data

(62) Division of application No. 09/388,524, filed on Sep. 2, 1999, now Pat. No. 6,084,105, which is a continuation of application No. PCT/EP98/01057, filed on Feb. 25, 1998.
(60) Provisional application No. 60/039,516, filed on Mar. 3, 1997.

(30) Foreign Application Priority Data

Mar. 14, 1997 (GB) .................................................. 9705316

(51) Int. Cl.⁷ ................................................. C07C 255/32
(52) U.S. Cl. ........................................... 558/390; 558/394
(58) Field of Search ................................... 558/390, 394; 546/279

(56) References Cited

U.S. PATENT DOCUMENTS 4,824,960   4/1989   Gallenkamp et al. ............... 548/362

FOREIGN PATENT DOCUMENTS

| | | |
|---|---|---|
| 0234119 | 9/1987 | (EP) . |
| 0295117 | 12/1988 | (EP) . |
| 92/13451 | 8/1992 | (WO) . |
| 93/06089 | 4/1993 | (WO) . |
| 97/32843 | 12/1997 | (WO) . |

OTHER PUBLICATIONS

Joucla et al, *Tetrahedron*, vol. 30, pp. 1121–1126 (1974).
Kim et al, *Tetrahedron Letters*, vol. 37, pp. 8771–8774 (1996).
March, *Advanced Organic Chemistry*, 3rd edition, p. 1062 (1985).

*Primary Examiner*—Joseph K. McKane
*Assistant Examiner*—Joseph Murray
(74) *Attorney, Agent, or Firm*—Burns, Doane, Swecker & Mathis, L.L.P.

(57) ABSTRACT

The invention relates to a process for the preparation of compounds having the formula (I)

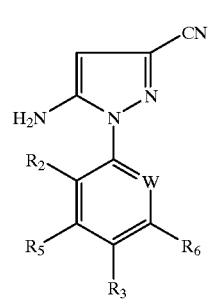

wherein W, $R_2$, $R_3$, $R_5$ and $R_6$ are as defined in the description, which are useful as intermediates in the synthesis of pesticidally active compounds.

18 Claims, No Drawings

PROCESSES FOR PREPARING PESTICIDAL INTERMEDIATES

This application is a division of U.S. application Ser. No. 09/388,524, filed Sep. 2, 1999, now U.S. Pat. No. 6,084,105, incorporated by reference herein in its entirety and relied upon, which is a continuation of International Patent Application No. PCT/EP98/01057, filed Feb. 25, 1998, and designating the United States, incorporated by reference herein in its entirety and relied upon, which claims the priority of U.S. Provisional Patent Application No. 60/039,516, filed Mar. 3, 1997 and United Kingdom Patent Application No. 97 05316.9, filed Mar. 14, 1997.

This invention relates to processes for preparing pesticidal intermediates, and to novel 2-arylhydrazonosuccinonitrile compounds and to 2-arylhydarylhydrazinosuccinonitrile compounds.

European Patent Publication Nos. 0295117 and 0234119 describe the preparation of pesticidally active phenylpyrazole compounds and of 5-amino-1-aryl-3-cyanopyrazole intermediate compounds used in their synthesis. Various methods for preparing these compounds are known. It is, however, desirable to provide improved methods for the preparation of these compounds and the intermediate compounds thereto.

Arylhydrazines are known to undergo Michael addition with electron deficient alkenes such as acrylonitrile in polar protic solvents such as alcohols, and subsequent oxidation in a basic medium affords 5-amino-1-arylpyrazoles as described, for example, in U.S. Pat. No. 4,824,960. However, the applicants are not aware of any literature reports describing the reaction of hydrazines with fumaronitrile. The oxidation of N,N¹-diarylhydrazines to azo compounds is known. N-Alkylhydrazines and N-arylhydrazines which are substituted on one nitrogen atom only are also oxidized to azo compounds but these are generally unstable, decomposing to nitrogen and hydrocarbons; see J. March, *Advanced Organic Chemistry*, 3rd edition, page 1062. Y. H. Kim and Y. Choi describe in *Tetrahedron Letters*, Vol 37, pages 8771–4, 1996, the palladium catalyzed dehydrogenation of alpha-hydrazinonitriles in the presence of cyclopentene to give hydrazonyl cyanides. However, the applicants are unaware of any other references concerning the oxidation of hydrazines to hydrazones. Moreover, the Kim and Choi publication is restricted to the oxidation of unsubstituted phenyl hydrazine derivatives and no suggestion is made that the oxidation of hydrazine derivatives of fumaronitrile may be achieved.

It is a first object of the present invention to provide a convenient process for preparing 5-amino-1-aryl-3-cyanopyrazole pesticidal intermediates which are obtained in high yield and high purity.

It is a further object of the present invention to provide processes for the preparation of 2-arylhydrazonosuccinonitrile compounds which may be used to prepare said 5-amino-1-aryl-3-cyanopyrazole pesticidal intermediates.

It is a yet further object of the present invention to provide a process for the preparation of 2-arylhydrazinosuccinonitrile compounds.

It is a still further object of the present invention to provide novel intermediates in the manufacture of pesticidally active compounds.

These and other objects of the invention will become apparent from the following description, and are achieved in whole or in part by the present invention.

In one aspect, the present invention provides a process for the preparation of a compound of formula (I) by the cyclization of a compound of formula (II), according to the reaction scheme Sc 1 indicated below:

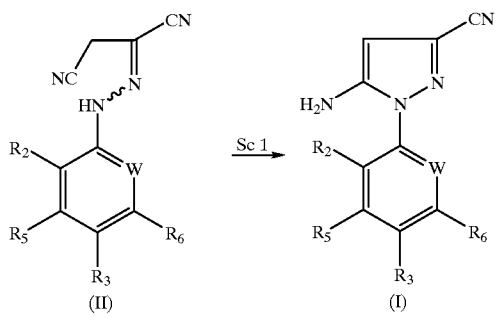

wherein W is nitrogen or —CR$_4$; R$_2$, R$_4$, R$_5$ and R$_6$ are independently selected from hydrogen, halogen, alkyl, haloalkyl, alkoxy, haloalkoxy, R$_7$S(O)$_n$—, nitro, cyano and —SF$_5$; and R$_3$ is as defined for R$_2$, or is phenyl optionally substituted by one to five members of the group consisting of halogen, alkyl, haloalkyl, alkoxy, haloalkoxy, R$_7$S(O)$_n$—, nitro, cyano and —SF$_5$, which are the same or different; R$_7$ is alkyl or haloalkyl; and n is 0, 1 or 2.

Unless otherwise specified in the present specification, 'alkyl' means straight- or branched-chain alkyl having from one to six carbon atoms (preferably one to three). Unless otherwise specified, 'haloalkyl' and 'haloalkoxy' are straight- or branched-chain alkyl or alkoxy, respectively, having from one to six carbon atoms (preferably one to three) substituted by one or more halogen atoms selected from fluorine, chlorine and bromine.

Preferred compounds of formula (I) are those having one or more of the following features: R$_2$ is halogen or hydrogen; R$_3$ represents halogen, haloalkyl (preferably trifluoromethyl), haloalkoxy (preferably trifluoromethoxy), R$_7$S(O)$_p$—, —SF$_5$, or phenyl substituted by one to three members of the group consisting of trifluoromethyl, trifluoromethoxy, difluoromethyl, —S(O)$_n$CF$_3$, dichlorofluoromethyl, chlorodifluoromethyl, chlorodifluoromethoxy, dichlorofluoromethoxy and halogen which may be the same or different; R$_4$ is halogen; and R$_5$ and R$_6$ are hydrogen.

Especially preferred compounds of formula (I) are those having one or more of the following features:

W represents —CR$_4$ and R$_4$ is halogen;

R$_3$ represents haloalkyl, haloalkoxy or —SF$_5$; and

R$_5$ and R$_6$ represent hydrogen.

Most preferably, the compound of formula (I) is 5-amino-3-cyano-1-(2,6-dichloro-4-trifluoromethylphenyl)pyrazole.

The above reaction Sc 1 to obtain compounds of formula (I) is generally performed in the presence of a base, which may be organic or inorganic. Examples of suitable organic bases are amines such as triethylamine or pyridine. Examples of suitable inorganic bases are alkali or alkaline earth metal hydroxides, acetates, carbonates or bicarbonates such as sodium hydroxide or sodium carbonate, or preferably ammonia (aqueous or gaseous). Generally, the molar ratio of the compound of formula (I):base is from about 1:10, to about 10:1. The reaction is optionally carried out in the presence of a phase transfer catalyst, for example, quaternary ammonium salts such as benzyl trimethylammonium chloride, tricaprylylmethylammonium chloride, tetramethylammonium chloride, tetra-n-propylammonium bromide, n-dodecyl trimethylammonium chloride, tetra-n-butylammonium chloride, and n-tetradecyl trinethylammonium bromide. The reaction is generally performed in a solvent, and suitable solvents include alcohols (preferably ethanol) or non water-miscible solvents, especially halogenated hydrocarbons such as dichloroethane or dichloromethane, non-miscible solvents being appropriate when a phase transfer catalyst is employed. Optionally water may be used as a co-solvent. The reaction temperature is generally from about −20 to about 50° C. and preferably from about 0 to about 20° C.

According to a further feature of the present invention, there is provided a process for the preparation of a compound of formula (II) by the oxidation of a compound of formula (III), according to the reaction scheme Sc 2 indicated below:

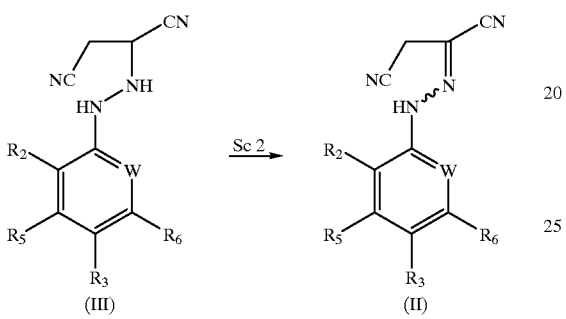

wherein W, $R_2$, $R_3$, $R_5$ and $R_6$ are as defined above.

The preferred compounds of formula (II) are as defined for the definition of W, $R_2$, $R_3$, $R_5$ and $R_6$ for compounds of formula (I) above. The most preferred compound of formula (II) is 2-(2,6-dichloro-4-trifluoromethylphenylhydrazono) succinonitrile.

Compounds of formula (II) may be obtained as a mixture of syn and anti isomers and all such forms are embraced by the present invention.

Suitable oxidants for the above reaction scheme Sc 2 to form compounds of formula (II) include quinones such as benzoquinone, peroxides such as hydrogen peroxide, hypohalites such as sodium hypochlorite, or an alkali metal hydroxide such as sodium hydroxide in the presence of air, or preferably a metal salt or oxide, for example, cupric chloride or mercuric oxide. The reaction is generally conducted in a solvent. Solvents suitable for use include aromatic halogenated or non-halogenated hydrocarbons such as toluene or chlorobenzene, nitriles such as acetonitrile or amides such as N,N-dimethylformamide. The reaction temperature is generally from about 20 to about 150° C., and preferably from about 50 to about 100° C.

According to a further feature of the present invention, there is provided a process for the preparation of a compound of formula (II) by the reaction of a compound of formula (IV), an enol thereof, or an enolate salt thereof, with a diazonium salt of formula (V) according to reaction scheme Sc 3 below:

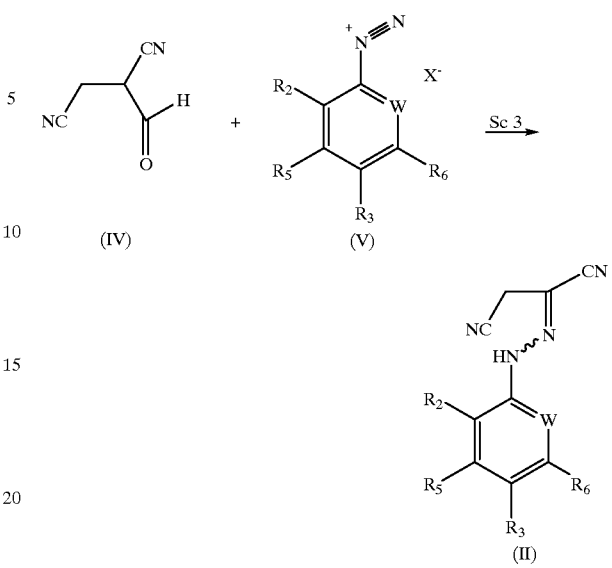

wherein W, $R_2$, $R_3$, $R_5$ and $R_6$ have the same meaning as defined above in reaction scheme Sc 1 and X is generally an anionic group from a mineral acid such as hydrogen sulfate or chloride.

The compound (IV) is generally in the form of an enolate salt, preferably an alkali metal salt, for example, the potassium or sodium enolate salt.

The above reaction Sc 3 to form a compound of formula (II) by the reaction of a compound of formula (IV) with a compound of formula (V) occurs by coupling and deformylation. When compound (IV) used is a metal enolate salt, the reaction is generally performed in the presence of sufficient excess of the mineral acid, for example, sulfuric acid or hydrochloric acid (which is generally present when the diazotization reaction is performed in the same pot), to convert the metal enolate into the free enol. Solvents such as acetic acid, water, halogenated hydrocarbons such as dichloromethane or dichloroethane, halogenated aromatics such as chlorobenzene, acetonitrile, N,N-dimethylformamide, or preferably an alcohol, for example ethanol, are generally employed. Optionally the reaction is conducted in the presence of a buffer such as sodium acetate. After the coupling stage, the reaction is generally completed by the addition of a weak base such as ammonium hydroxide solution to give a weakly basic solution, for example having a pH of about 8. The reaction temperature is generally from about −20 to about 50° C. and preferably from about 0 to about 20° C.

The diazonium salt above of formula (V) is generally prepared in situ by diazotizing a compound of formula (Va):

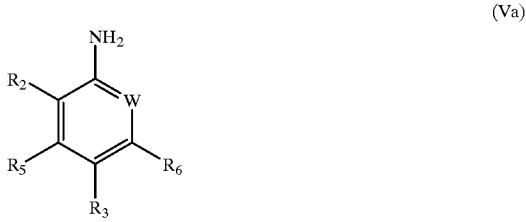

wherein W, $R_2$, $R_3$, $R_5$ and $R_6$ have the same meaning as defined above, using conditions known in the literature and generally using a molar equivalent of sodium nitrite and a mineral acid such as hydrochloric acid or sulfuric acid.

According to a further feature of the present invention, compounds of formula (II) wherein W, $R_2$, $R_3$, $R_5$ and $R_6$ have the same meaning as defined above in reaction scheme Sc 1 may also be prepared by the reaction of a compound of formula (VI):

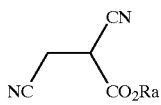

(VI)

wherein Ra is alkyl, preferably ethyl, with a diazonium salt of formula (V) wherein W, $R_2$, $R_3$, $R_5$, $R_6$ and X are as defined above.

The reaction conditions used are the same as those described above for reaction scheme Sc 3 above.

According to a further feature of the present invention, compounds of formula (III) above may be prepared by the reaction of an arylhydrazine of formula (VII) with a compound of formula (VIII), according to reaction scheme Sc 4 indicated below:

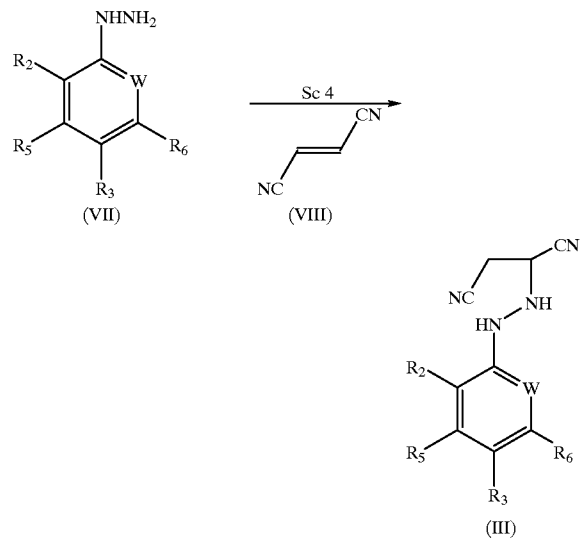

wherein W, $R_2$, $R_3$, $R_5$ and $R_6$ have the same meanings as defined above in reaction scheme Sc 1.

Compounds of formula (VIII) are known and may be used in the form of the cis-isomer maleonitrile or, preferably, the trans isomer fumaronitrile. Optionally, a mixture of both isomers may be used. Arylhydrazines of formula (VII) are known or may be prepared by known methods.

Preferred compounds of formula (III) have the same values of W, $R_2$, $R_3$, $R_5$ and $R_6$ as preferred above for compounds of formula (I). Most preferably, the compound of formula (III) is 2-(2,6-dichloro-4-trifluoromethylphenylhydrazino)succinonitrile.

The above reaction to form compounds of formula (III) may be performed in a variety of solvents, polar solvents being preferred, for example alcohols. Polar aprotic solvents such as N-methylpyrrolidone, N,N-dimethylformamide or dimethylsulfoxide are especially preferred. In another preferred aspect, the reaction is performed in the absence of solvent by heating a mixture of compounds of formula (VII) and (VIII).

Optionally, a catalyst such as a tetra-alkylammonium salt, for example, N-benzyltrimethylammonium hydroxide, or alanine may also be present in the reaction.

The reaction temperature is generally from about 20 to about 150° C., and preferably from about 80 to about 100° C.

The reaction may be carried out using a molar ratio of a compound of formula (VIII) to a compound of formula (VII) of from about 1:10 to about 10:1, and preferably from about 1:1 to about 5:1, even more preferably about 1.1 to 1.

Compounds of formula (II) and (III) above are novel and therefore constitute a further feature of the present invention.

The following non-limiting examples illustrate the invention. NMR spectra are recorded using deuterochloroform as solvent.

Hplc means high performance liquid chromatography, m.p. means melting point.

EXAMPLE 1

Preparation of 5-amino-3-cyano-1-(2,6-dichloro-4-trifluoromethylphenyl)pyrazole (Reaction scheme Sc 1)

Ammonia (20 microliters of an 8% ammonia solution in water) was added to a mixture of 2-(2,6-dichloro-4-trifluoromethylphenylhydrazono)succinonitrile (0.077 g) in ethanol (1 ml) and water (0.2 ml) at 0° C. After 10 minutes, the mixture was extracted (dichloromethane) and evaporated to give the title compound (0.076 g, 97% yield). Purity 98% (by hplc).

EXAMPLE 2

Preparation of 5-amino-3-cyano-1-(2,6-dichloro-4-trifluoromethylphenyl)pyrazole (Reaction scheme Sc 1)

A solution of 2-(2,6-dichloro-4-trifluoromethylphenylhydrazono)succinonitrile (1.0 g) and sodium bicarbonate (40 ml of a saturated aqueous solution) and dichloromethane (915 ml) was stirred at 20° C. for 3 hours at pH 9. Sodium carbonate solution was then added until the pH was 11 and the stirring continued overnight. A small amount of sodium hydroxide solution was added to give a pH of 12, followed three hours later by a small quantity of Aliquat 336 (trademark, tricaprylylmethylammonium chloride), and after 2 hours the reaction was complete. A dichloromethane extract was washed (water and brine), dried (sodium sulfate) and evaporated to give the title compound.

EXAMPLE 3

Preparation of 2-(2,6-dichloro-4-trifluoromethylphenylhydrazono)succinonitrile (Reaction Scheme Sc 2)

A mixture of 2-(2,6-dichloro-4-trifluoromethylphenylhydrazino)succinonitrile (0.323 g) and cupric chloride (0.175 g) was heated in chlorobenzene at 60° C. for 6 hours. After filtration and evaporation, the title compound and 5-amino-3-cyano-1-(2,6-dichloro-4-trifluoromethylphenyl)pyrazole were obtained as a 7:1 mixture. Column chromatography on silica gel eluting with dichloromethane gave the pure title compound, obtained as a mixture of syn and anti isomers, NMR (anti isomer) 3.6 (s, 2H), 7.57 (s, 2H), 8.82 (s, 1H, exchangeable with $D_2O$), NMR (syn isomer) 3.56 (s, 2H), 7.59 (s, 2H), 8.27 (s, 1H, exchangeable with $D_2O$).

EXAMPLE 4

Preparation of 2-(2,6-dichloro-4-trifluoromethylphenylhydrazono)succinonitrile (Reaction scheme Sc 3)

Sodium nitrite (3.9 g) was added to stirred concentrated sulfuric acid (12.8 ml) and heated at 80° C. until dissolved. Acetic acid (25 ml) was added at 30° C. A mixture of 2,6-dichloro-4-trifluoromethylphenylaniline (10.0 g) and acetic acid (25 ml) was added over 10 minutes at 20° C. maintaining below 25° C. The mixture was heated at 55° C. for 50 minutes, and further sodium nitrite (0.65 g) and acetic acid (10 ml) added, and after 20 minutes heated to 70° C. and sulfuric acid (2.8 ml) added. After 20 minutes the cooled mixture was added to a mixture of 2-hydroxymethylenesuccinonitrile potassium salt (7.6 g) and sodium acetate (35.6 g) in water and acetic acid (70 ml) at 10° C. After warming to 20° C. during 1 hour, dichloromethane was added followed by ammonium hydroxide solution (210 ml) to give a pH of 8. The organic phase was separated, washed (water and brine), dried (sodium sulfate) and evaporated to give the title compound as a red-brown solid (18.1 g). Recrystallization from hexane/t-butyl methyl ether) gave the pure title compound (6.85 g), m.p. 80–82° C., NMR 3.6 (s, 2H), 7.66 (s, 2H), 9.03 (s, 1H exchangeable with $D_2O$).

EXAMPLE 5

Preparation of 2-(2,6-dichloro-4-trifluoromethylphenylhydrazino)succinonitrile (Reaction Scheme Sc 4)

A mixture of 2,6-dichloro-4-trifluoromethylphenylhydrazine (1.0 g) and fumaronitrile (1.0 g) in dimethylsulfoxide (10 ml) was heated at 100° C. for 7 hours. The cooled mixture was diluted with water and extracted (ether) to give, after evaporation and crystallization from dichloromethane/hexane, the title compound (0.828 g, 63%), m.p. 101–102° C.

EXAMPLE 6

Preparation of 2-(phenylhydrazino)succinonitrile (Reaction Scheme Sc 4)

A mixture of phenylhydrazine (4.29 g) and fumaronitrile (3.1 g), where the phenylhydrazine served as a solvent, was heated at 75–80° C. for 20 hours. Purification by flash chromatography on silica gel and crystallization from dichloromethane/hexane gave the title compound (3.29 g, 45%), m.p. 97–98° C.

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

What is claimed is:
1. A compound having the formula (II):

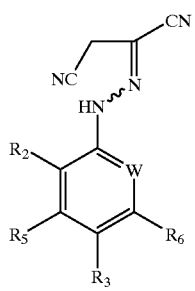

(II)

wherein
W is nitrogen or —$CR_4$;
$R_2$, $R_4$, $R_5$ and $R_6$ are independently selected from hydrogen, halogen, $C_{1-6}$ alkyl, $C_{1-6}$ haloalkyl, $C_{1-6}$ alkoxy, $C_{1-6}$ haloalkoxy, $R_7S(O)_n$—, nitro, cyano and —$SF_5$;
$R_3$ is hydrogen, halogen, $C_{1-6}$ alkyl, $C_{1-6}$ haloalkyl, $C_{1-6}$ alkoxy, $C_{1-6}$ haloalkoxy, $R_7S(O)_n$—, nitro, cyano, —$SF_5$, or phenyl substituted by one to five members of the group consisting of halogen, $C_{1-6}$ alkyl, $C_{1-6}$ haloalkyl, $C_{1-6}$ alkoxy, $C_{1-6}$ haloalkoxy, $R_7S(O)_n$—, nitro, cyano and —$SF_5$, which are the same or different;
$R_7$ is $C_{1-6}$ alkyl or $C_{1-6}$ haloalkyl; and
n is 0, 1 or 2.
2. A compound according to claim 1, having one or more of the following features:
$R_2$ is halogen or hydrogen;
$R_3$ represents halogen, $C_{1-6}$ haloalkyl, $C_{1-6}$ haloalkoxy, $R_7S(O)_p$—, —$SF_5$, or phenyl substituted by one to three members of the group consisting of trifluoromethyl, trifluoromethoxy, difluoromethyl, —$S(O)_nCF_3$, dichlorofluoromethyl, chlorodifluoromethyl, chlorodifluoromethoxy, dichlorofluoromethoxy and halogen, which are the same or different;
$R_4$ is halogen;
$R_5$ and $R_6$ are hydrogen.
3. The compound according to claim 1, which is 2-(2,6-dichloro-4-trifluoromethylphenylhydrazono)succinonitrile.
4. A process for the preparation of a compound of formula (II) as defined in claim 1, said process comprising oxidizing a compound having the formula (III):

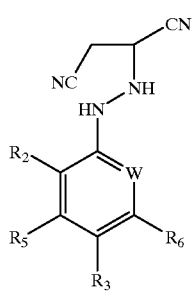

(III)

wherein W, $R_2$, $R_3$, $R_5$ and $R_6$ are as defined in claim 1, with an oxidant.
5. A process according to claim 4, wherein the compound of formula (III) has one or more of the following features:

$R_2$ is halogen or hydrogen;

$R_3$ represents halogen, $C_{1-6}$ haloalkyl, $C_{1-6}$ haloalkoxy, $R_7S(O)_p$—, —$SF_5$, or phenyl substituted by one to three members of the group consisting of trifluoromethyl, trifluoromethoxy, difluoromethyl, —$S(O)_nCF_3$, dichlorofluoromethyl, chlorodifluoromethyl, chlorodifluoromethoxy, dichlorofluoromethoxy and halogen, which are the same or different;

$R_4$ is halogen;

$R_5$ and $R_6$ are hydrogen.

6. A process according to claim 4, wherein the oxidant is selected from a quinone; a peroxide; a hypohalite; an alkali metal hydroxide in the presence of air; a metal salt; and a metal oxide.

7. A process according to claim 4, comprising oxidizing 2-(2,6-dichloro-4-trifluoromethylphenylhydrazino)succinonitrile, with an oxidant, to afford 2-(2,6-dichloro-4-trifluoromethylphenylhydrazino)succinonitrile.

8. A process according to claim 7, wherein the oxidant is cupric chloride.

9. A process for the preparation of a compound of formula (II) as defined in claim 1, said process comprising reacting an enolate salt of a compound having the formula (IV):

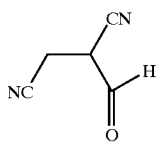

(IV)

with a diazonium salt having the formula (V):

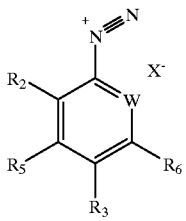

(V)

wherein W, $R_2$, $R_3$, $R_5$ and $R_6$ are as defined in claim 1 and X is hydrogen sulfate or chloride.

10. A process according to claim 9, wherein the compound of formula (V) has one or more of the following features:

$R_2$ is halogen or hydrogen;

$R_3$ represents halogen, $C_{1-6}$ haloalkyl, $C_{1-6}$ haloalkoxy, $R_7S(O)_p$—, —$SF_5$, or phenyl substituted by one to three members of the group consisting of trifluoromethyl, trifluoromethoxy, difluoromethyl, —$S(O)_nCF_3$, dichlorofluoromethyl, chlorodifluoromethyl, chlorodifluoromethoxy, dichlorofluoromethoxy and halogen, which are the same or different;

$R_4$ is halogen;

$R_5$ and $R_6$ are hydrogen.

11. A process according to claim 9, wherein the diazonium salt of formula (V) is prepared in situ by diazotizing the corresponding compound of the formula (Va):

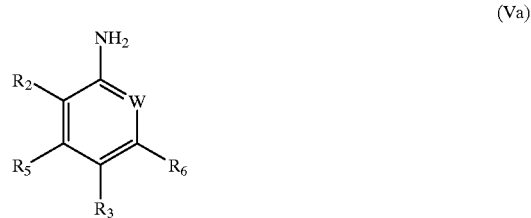

(Va)

wherein W, $R_2$, $R_3$, $R_5$ and $R_6$ are as defined in claim 9.

12. A process according to claim 11, wherein the compound of formula (Va) is 2,6-dichloro-4-trifluoromethylphenylalanine.

13. A compound having the formula (III):

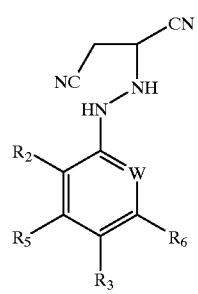

(III)

wherein W is nitrogen or —$CR_4$;

$R_2$, $R_4$, $R_5$ and $R_6$ are independently selected from hydrogen, halogen, $C_{1-6}$ alkyl, $C_{1-6}$ haloalkyl, $C_{1-6}$ alkoxy, $C_{1-6}$ haloalkoxy, $R_7S(O)_n$—, nitro, cyano and —$SF_5$;

$R_3$ is hydrogen, halogen, $C_{1-6}$ alkyl, $C_{1-6}$ haloalkyl, $C_{1-6}$ alkoxy, $C_{1-6}$ haloalkoxy, $R_7S(O)_n$—, nitro, cyano, —$SF_5$, or phenyl substituted by one to five members of the group consisting of halogen, $C_{1-6}$ alkyl, $C_{1-6}$ haloalkyl, $C_{1-6}$ alkoxy, $C_{1-6}$ haloalkoxy, $R_7S(O)_n$—, nitro, cyano and —$SF_5$, which are the same or different;

$R_7$ is $C_{1-6}$ alkyl or $C_{1-6}$ haloalkyl; and n is 0, 1 or 2.

14. A compound according to claim 13, having one or more of the following features:

$R_2$ is halogen or hydrogen;

$R_3$ represents halogen, $C_{1-6}$ haloalkyl, $C_{1-6}$ haloalkoxy, $R_7S(O)_p$—, —$SF_5$, or phenyl substituted by one to three members of the group consisting of trifluoromethyl, trifluoromethoxy, difluoromethyl, —$S(O)_nCF_3$, dichlorofluoromethyl, chlorodifluoromethyl, chlorodifluoromethoxy, dichlorofluoromethoxy and halogen, which are the same or different;

$R_4$ is halogen;

$R_5$ and $R_6$ are hydrogen.

15. The compound according to claim 13, which is 2,6-dichloro-4-trifluoromethylphenylhydrazine.

16. A process for the preparation of a compound of formula (III) as defined in claim 13, said process comprising reacting an arylhydrazine having the formula (VII):

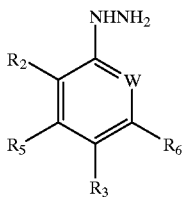

(VII)

wherein W, $R_2$, $R_3$, $R_5$ and $R_6$ are as defined in claim 13, with a compound of formula (VIII):

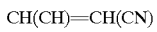

(VIII).

17. A process according to claim 16, wherein the compound of formula (VII) has one or more of the following features:

$R_2$ is halogen or hydrogen;

$R_3$ represents halogen, $C_{1-6}$ haloalkyl, $C_{1-6}$ haloalkoxy, $R_7S(O)_p$—, —$SF_5$, or phenyl substituted by one to three members of the group consisting of trifluoromethyl, trifluoromethoxy, difluoromethyl, —$S(O)_nCF_3$, dichlorofluoromethyl, chlorodifluoromethyl, chlorodifluoromethoxy, dichlorofluoromethoxy and halogen, which are the same or different;

$R_4$ is halogen; and $R_5$ and $R_6$ are hydrogen.

18. A process according to claim 16, comprising reacting 2-(2,6-dichloro-4-trifluoromethylphenylhydrazine with fumaronitrile to afford 2-(2,6-dichloro-4-trifluoromethylphenylhydrazino)succinonitrile.

* * * * *